United States Patent
Wang et al.

(10) Patent No.: US 10,421,901 B2
(45) Date of Patent: Sep. 24, 2019

(54) PREPARATION METHOD OF NEAR-INFRARED SILVER SULFIDE QUANTUM DOTS

(71) Applicant: SUZHOU INSTITUTE OF NANO-TECH AND NANO-BIONICS, CHINESE ACADEMY OF SCIENCES, Suzhou (CN)

(72) Inventors: Qiangbin Wang, Suzhou (CN); Yejun Zhang, Suzhou (CN)

(73) Assignee: Suzhou Institute of Nano-Tech and Nano-Bionics, Chinese Academy of Sciences (CN)

(*) Notice: Subject to any disclaimer, the term of this patent is extended or adjusted under 35 U.S.C. 154(b) by 522 days.

(21) Appl. No.: 14/955,736

(22) Filed: Dec. 1, 2015

(65) Prior Publication Data

US 2016/0083647 A1    Mar. 24, 2016

Related U.S. Application Data

(63) Continuation of application No. 13/985,731, filed as application No. PCT/CN2012/000167 on Feb. 10, 2012, now abandoned.

(30) Foreign Application Priority Data

May 30, 2011    (CN) .......................... 2011 1 0142093

(51) Int. Cl.
*A61K 49/00* (2006.01)
*C09K 11/02* (2006.01)
*G01N 33/58* (2006.01)
*C09K 11/58* (2006.01)
*C07F 1/00* (2006.01)

(52) U.S. Cl.
CPC ........ *C09K 11/025* (2013.01); *A61K 49/0067* (2013.01); *C07F 1/005* (2013.01); *C09K 11/582* (2013.01); *G01N 33/588* (2013.01); *A61K 49/0013* (2013.01)

(58) Field of Classification Search
None
See application file for complete search history.

(56) References Cited

U.S. PATENT DOCUMENTS

2009/0315446 A1    12/2009    Murase et al.

FOREIGN PATENT DOCUMENTS

| CN | 101508416 | 8/2009 |
|---|---|---|
| CN | 101723311 | 6/2010 |
| CN | 101805606 | 8/2010 |
| CN | 101857276 A | 10/2010 |
| CN | 102277157 | 12/2011 |
| JP | 2003535063 | 11/2003 |
| JP | 2006515418 | 5/2006 |

OTHER PUBLICATIONS

Pileni et al. (J. Phys. Chem. B 1998, 102, 4104-4109).*
Motte et al. (J. Phys. Chem. 1995, 99, 16425-46429).*
Wilson et al. (Chem. Mater. 2010, 22, 6361-6369).*
Michael C. Brelle et al: "Synthesis and Ultrafast Study of Cysteine- and Glutathione-Capped Ag 2 S Semiconductor Colloidal Nanoparticles", The Journal of Physical Chemistry A, vol. 103, No. 49, Dec. 1, 1999 (Dec. 1, 1999), pp. 10194-10201, XP055153558, ISSN: 1089-5639, DOI: 10.1021/jp991999j.
J. Xiang et al: "L-Cysteine-Assisted Synthesis and Optical Properties of Ag2S Nanospheres", Journal of Physical Chemistry C, vol. 112, No. 10, Mar. 13, 2008 (Mar. 13, 2008), pp. 3580-3584, XP055153561, ISSN: 1932-7447, DOI: 10.1021/jp710597j.
Chungui Tian et al: "'One-step' controllable synthesis of Ag and Ag2S nanocrystals on a large scale", Nanotechnology, IOP, Bristol, GB, vol. 17, No. 22, Nov. 28, 2006, (Nov. 28, 2006), pp. 5681-5685, XP020104311, ISSN: 0957-4484, DOI: 10.1088/0957-4484/17/22/024.
Interface Reaction for the Self-Assembly of Silver nanocrystals under Microwaved-Assisted Solvothermal Conditions, Gao et al., Chem. Mater. 2005, 856-860.
Controllable Assembly of Ordered Semiconductor Ag2S Nanostructures, Gao et al., Nanoletters, 2003, vol. 3, No. 1, 85-88.
International Search Report issued in PCT/CN2012/000167 dated May 24, 2012.

* cited by examiner

*Primary Examiner* — Michael G. Hartley
*Assistant Examiner* — Melissa J Perreira
(74) *Attorney, Agent, or Firm* — Gesmer Updegrove LLP

(57) ABSTRACT

Provided is a preparation method of near-infrared silver sulfide quantum dots. The silver sulfide quantum dots have hydrophilic groups derived from a mercapto-containing hydrophilic reagent attached on the surface thereof, and the hydrophilic reagent is any one of mercaptoacetic acid, mercaptopropionic acid, cysteine, cysteamine, thioctic acid and ammonium mercaptoacetate or any combination thereof. The silver sulfide quantum dots have high fluorescence yield, good fluorescence stability, good biocompatibility and uniform sizes. The preparation method has moderate reaction conditions, simple operation, short production cycle, good reproducibility and is easy to control. The silver sulfide quantum dots can be used in the application of cellular imaging and biological tissue imaging.

4 Claims, 3 Drawing Sheets

PREPARATION METHOD OF NEAR-INFRARED SILVER SULFIDE QUANTUM DOTS

CROSS-REFERENCE TO RELATED APPLICATION

The present application is a continuation application of U.S. patent application Ser. No. 13/985,731 filed on Aug. 15, 2013 by the same inventors, and claims the priority benefit of Chinese application No. 201110142093.8 filed on May 30, 2011. The entire contents of those applications are incorporated herein by reference.

TECHNICAL FIELD

The present invention relates to the technical field of material chemistry and biology. In particular, the present invention relates to near-infrared silver sulfide quantum dots, a preparation method thereof and a biological application thereof.

BACKGROUND

As a fundamental method of biomedical research, the fluorescence labeling and detecting technologies play an important role in the studies at subcellular level, cellular level and in vivo level. In in vivo imaging, the fluorescence imaging technology with near-infrared quantum dots has many unique advantages. For example, it has deeper depth of tissue pentration, and can overcome the defect that the deep tissue imaging with visible-light quantum dots is susceptible to the background fluorescence. Thus it draws broad attention in medical diagnostics, molecular biology, cellular biology and the like. Currently, all the common near-infrared quantum dots contain toxic elements such as Cd, Hg, Pb and the like. Silver sulfide ($Ag_2S$) quantum dots with low toxicity or even without toxicity exhibiting near-infrared fluorescence have been reported (Near-infrared photoluminescent $Ag_2S$ quantum dots from a single source precursor. J. Am. Chem. Soc., 2010, 132, 1470), but the particles are relatively large and the near-infrared fluorescence intensity is not strong enough. Other literatures regarding $Ag_2S$ have not given the report regarding fluorescence. Moreover, the $Ag_2S$ reported in those literatures has poor homogeneity and dispersity and is made by complex preparation methods. Furthermore, the surface functionalization of quantum dots, i.e. transformation from hydrophobic form into hydrophilic form, to make the quantum dots to be used for biomedical research, has been reported in many literatures. However, the surface functionalization processes reported is substantially not suitable for $Ag_2S$ quantum dots, because all the $Ag_2S$ quantum dots have superlattice structure and it is difficult to modify the superlattice with conventional processes. Furthermore, reagents with strong oxidability are not suitable for the transformation of $Ag_2S$ to its hydrophilic form. Therefore, it is of great significance to develop a method for preparation and surface functionalization of $Ag_2S$ quantum dots, which is simple process and can produce high quality of $Ag_2S$ quantum dots with uniform particle sizes, good particle dispersity, high fluorescence intensity and good reproducibility, so that the $Ag_2S$ quantum dots can be used in the biological field.

SUMMARY

To overcome the above problems, an object of the invention is to provide near-infrared silver sulfide quantum dots.

The near-infrared silver sulfide quantum dots have the advantages such as high fluorescence yield, fluorescence stability, uniform sizes, easy preparation process and the like, and may further have good biocompatibility after surface functionalization, which makes them useful in biological imaging.

The near-infrared silver sulfide quantum dots according to the invention have hydrophilic groups attached to the surface thereof, which are derived from a mercapto-containing hydrophilic reagent. The hydrophilic reagent is any one of mercaptoacetic acid, mercaptopropionic acid, cysteine, cysteamine, thioctic acid and ammonium mercaptoacetate or any combination thereof.

In order to overcome the above problems, another object of the invention is to provide a method for preparation of near-infrared silver sulfide quantum dots, wherein the method comprises the following steps:

1) preparing hydrophobic silver sulfide quantum dots; and
2) reacting the hydrophobic silver sulfide quantum dots obtained in step 1) with equivalent or excessive amount of mercapto-containing hydrophilic reagent in polar organic solvent, so that the surface of the silver sulfide quantum dots is attached with hydrophilic groups, to obtain the near-infrared silver sulfide quantum dots. In the invention, the hydrophilic silver sulfide quantum dots as prepared have good performance, provided that the mole number of the mercapto-containing hydrophilic reagent is more than or equal to that of the hydrophobic silver sulfide quantum dots. The ratio of the mole number of the mercapto-containing hydrophilic reagent to that the hydrophobic silver sulfide quantum dots can be adjusted depending on the actual requirement during the preparation process, so that the objects of the invention can be achieved.

The hydrophilic reagent is any one of mercaptoacetic acid, mercaptopropionic acid, cysteine, cysteamine, thioctic acid and ammonium mercaptoacetate or any combination thereof.

In the method for preparation of near-infrared silver sulfide quantum dots according to the invention, the polar organic solvent in step 2) comprises, but not limited to, any one of ethanol, methanol, acetone and 1-methyl-2-pyrrolidone or any combination thereof. The pH value of the mixed system of the hydrophobic silver sulfide quantum dots and the mercapto-containing hydrophilic reagent in step 2) is adjusted to 7-14, and the mixed system is reacted in the polar organic solvent at 2-80° C. for 3 or more hours. In the present invention, the hydrophilic silver sulfide quantum dots as prepared have good performances, provided that the reaction time is more than or equal to 3 hours. The reaction time can be adjusted depending on the actual requirement during the preparation process, so that the objects of the invention can be achieved.

Preferably, the method for preparation of the hydrophobic silver sulfide quantum dots in step 1) comprises the following steps:

1-1) heating a mixed reaction system containing a silver source and a long chain thiol to 80-350° C. in a closed environment to react sufficiently; and 1-2) naturally cooling the mixed reaction system to room temperature, then adding a polar solvent, centrifuging and washing to obtain the hydrophobic near-infrared silver sulfide quantum dots;

wherein the silver source comprises one or more of silver nitrate, silver diethyldithiocarbamate, silver dihydrocarbyldithiophosphate, dioctyl silver sulfosuccinate, silver thiobenzoate, silver acetate, silver dodecanoate, silver tetradecanoate and silver octadecanoate; and the long chain thiol comprises one or more of octanethiol, undecanethiol, dodecanethiol, tridecanethiol, tetradecanethiol, pentadecanethiol, hexadecanethiol, octadecanethiol, eicosanethiol, hexanethiol, 1,6-hexanedithiol, and 1,8-octanedithiol.

In the method for preparation of near-infrared silver sulfide quantum dots according to the invention, it is preferred that the mixed reaction system in step 1-2) further comprises a surfactant with coordination property, which is any one of a long chain alkyl acid, alkylamine, a long chain alcohol, and a long chain thiol and ether or any combination thereof; and the mixture reaction system is placed in a closed environment to react. More preferably, in step 2), the hydrophobic silver sulfide quantum dots were reacted with the mercapto-containing hydrophilic reagent under the condition of continuous stirring and/or vibrating and/or sonicating in the polar organic solvent at 2-80° C. for 3 or more hours.

In the method for preparation of near-infrared silver sulfide quantum dots according to the invention, the near-infrared silver sulfide quantum dots prepared by the method described in the invention have monoclinic structure and the particle sizes thereof are below 8 nm.

The use of the near-infrared silver sulfide quantum dots according to the invention in the imaging of biological tissues is provided.

In the invention, the silver source and the long chain thiol are used as reactants, and the hydrophobic silver sulfide quantum dots are nucleated and grown in reaction systems in the presence of the surfactant with different coordination properties, to obtain the hydrophobic silver sulfide quantum dots, wherein the long chain thiol provides the sulfur source and can be used as solvent and surfactant. Then the surface functionalization of the hydrophobic silver sulfide quantum dots as prepared is conducted with the mercapto-containing hydrophilic reagent. Since the mercapto groups have an excellent binding ability with silver, they can replace other groups on the surface of the silver sulfide quantum dots, resulting in the near-infrared silver sulfide quantum dots with low toxicity, good biocompatibility and high fluorescence yield. The difference from the modification of the hydrophobic material to the hydrophilic material in the prior art is that the $Ag_2S$ quantum dots firstly prepared according to the invention, which have superlattice structure, can not be modified to hydrophilic $Ag_2S$ quantum dots by the experimental conditions for modification in the prior art due to this special structure. Through numerous experiments, summaries in combination with the experiences of the inventor, it has been found that the modification time, which has a significant impact on the modification effect, is a key experimental condition when the $Ag_2S$ quantum dots with the special structure are modified. Moreover, it has been found that better modification effect can be achieved when the modification time is equal to or more than 3 hours. The longer the time is, the better the modification effect is. Therefore, the time may be adjusted depending on the actual requirement during the preparation process. However, the objects of the invention can be achieved, provided that the time is 3 or more hours. In addition, the hydrophilic $Ag_2S$ quantum dots after modification are monodispersed, do not aggregate, have good hydrophilicity and stability, and can be used for cellular imaging, and in particular, for the in vivo imaging.

Specifically, the process of the invention comprises the following steps: mixing a silver source, a long chain thiol and a suitable surfactant; placing the mixture into a closed device and heating to an appropriate temperature for a certain time to conduct nucleation and growth; then cooling naturally and adding excessive amount of ethanol; centrifuging and washing to obtain the hydrophobic silver sulfide quantum dots; then mixing the prepared hydrophobic silver sulfide quantum dots, a certain amount of mercapto-containing hydrophilic reagent and ethanol; and stirring, vibrating or sonicating the mixture to react completely; centrifuging and washing with water to obtain a low toxic near-infrared silver sulfide quantum dots with a good biocompatibility and high fluorescence yield which can be used for cellular imaging.

In addition, the above technical solution may further comprise the following embodiments:

1. Different silver sources, different long chain thiols, different surfactants, different reaction temperatures and different reaction time can be used in the reaction to adjust the sizes of the silver sulfide nano particles. For example, it is possible to enlarge particle sizes by raising the temperature or extending the reaction time.

2. The dispersity of the functionalized $Ag_2S$ quantum dots in aqueous solution can be changed by adjusting the pH value (a better dispersity is obtained at pH 7-14). And the emission peak can be adjusted depending on the different modification by different mercapto-containing hydrophilic reagent in the reaction.

Compared with the prior art, the advantages of the technical solution of the invention are that the process of the invention has moderate reaction conditions, simple operation, short production cycle, and good reproducibility, and is easy to be controlled. The $Ag_2S$ quantum dots prepared have high fluorescence yield, good fluorescence stability, excellent biocompatibility and homogeneous sizes, and can be used for in vitro cellular imaging and in vivo imaging.

DESCRIPTION OF EMBODIMENTS

The preparation process of the invention is explained in detail by the specific examples below.

EXAMPLE 1

Figure 1:
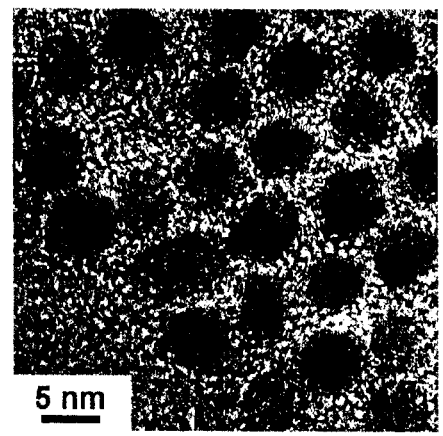
FIG. 1 is the TEM image of the hydrophobic $Ag_2S$ quantum dots in Example 1.
Figure 2:
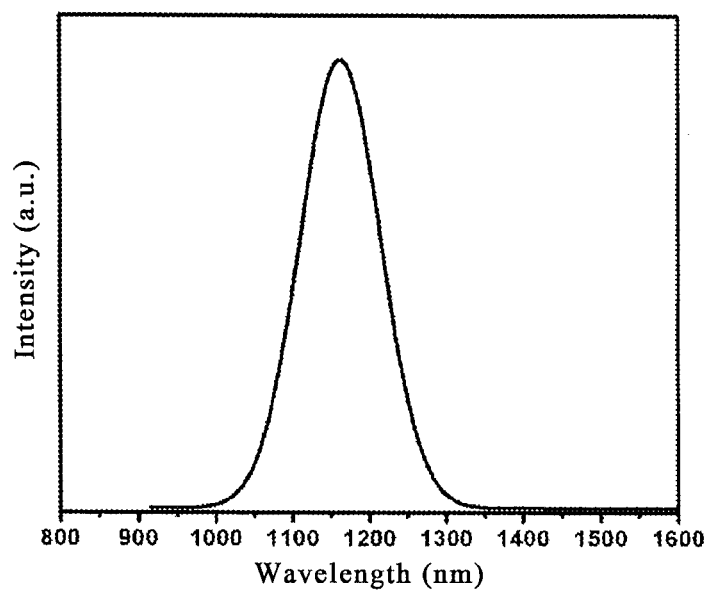
FIG. 2 is the near-infrared fluorescence spectrum of the hydrophobic $Ag_2S$ quantum dots in Example 1.
Figure 3:
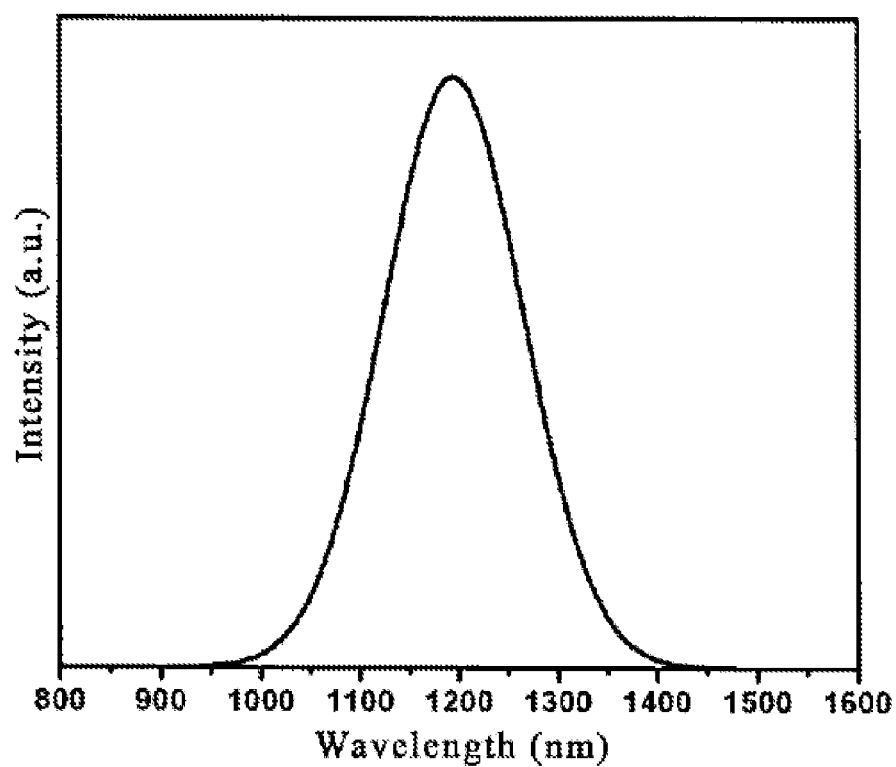
FIG. 3 is the near-infrared fluorescence spectrum of the hydrophilic $Ag_2S$ quantum dots in Example 1.
Figure 4:
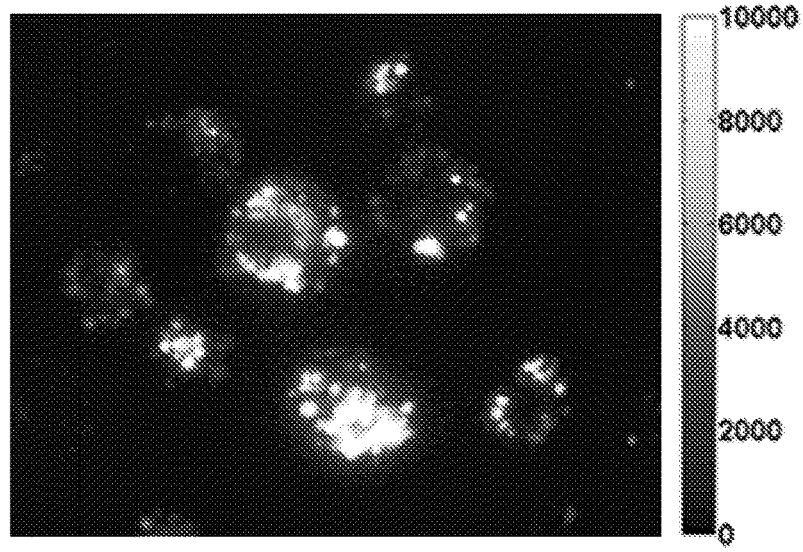
FIG. 4 is the fluorescence photograph of cells specifically labeled with the near-infrared quantum dots of silver sulfide in Example 1.
Figure 5:
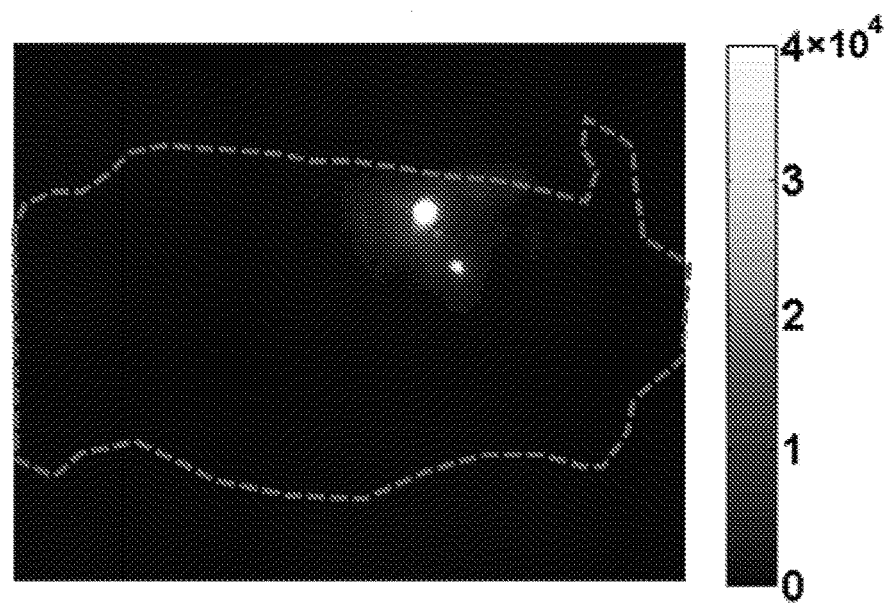
FIG. 5 is the fluorescence photograph of the tumor in a living mouse specifically labeled with the near-infrared quantum dots of silver sulfide.

0.1 mmol of silver diethyldithiocarbamate and 10 g of dodecanethiol were mixed in a flask, and heated to 200° C. under a $N_2$ atmosphere for 1 h. 50 mL of anhydrous ethanol was added to the solution after the solution was cooled naturally to room temperature, and then the resultant mixture was centrifuged, washed and dispersed in cyclohexane. The sample obtained was identified to be monoclinic $Ag_2S$ quantum dots by X ray diffraction and transmission electron microscopy (the particle size thereof is about 5 nm, as shown in FIG. 1), which has a good near-infrared fluorescence emission spectrum, as shown in FIG. 2. 0.15 g of thioctic acid was added to the above cyclohexane dispersion, and equal volume of anhydrous ethanol was added, then the resultant mixture was sonicated in an ultrasonic cleaner for 4 h, centrifuged and washed with deionized water to obtain water-soluble $Ag_2S$ quantum dots with particle sizes of about 5 nm which still have very strong fluorescence emission, as shown in FIG. 3. 0.25 mg of the above $Ag_2S$ quantum dots were dispersed in 100 µL of dimethyl sulfoxide (DMSO), and 50 µL of DMSO solution containing 0.01 mmol of NHS was mixed with the above solution. Then 50 µL of DMSO solution containing 0.01 mmol of EDC was added to the above mixed solution, and the resultant mixture was packed with aluminum foil, stirred for 1 h, centrifuged and further dispersed in 100 µL, of DMSO. The mixed solution of 15 µL of 2 mg/mL Erbitux and 185 µL of 1× PBS was added to 100 µL of $Ag_2S$/DMSO mixed solution, and the resultant mixture was reacted in darkness at 4° C. for 12 h, then centrifuged at 400 g for 4 min, and then the supernatant was taken. MDA-MB-468 cells were added to the mixed solution of 100 µL of the above supernatant and 100 µL of 1× PBS, coloured at 4° C. for 2 h, and then washed 3 times with 1× PBS solution. It can clearly be seen that the luminescence was given by $Ag_2S$ quantum dots in cells by exciting with 658 nm laser, using 1100 nm filter, and photographing with a 2D InGaAs camera (see FIG. 4).

EXAMPLE 2

0.1 mmol of silver nitrate, 8 g of dodecanethiol and 5.4 g of oleylamine were mixed in a three-necked flask, and heated to 180° C. under air for 1 h. After the solution was cooled naturally to room temperature, 50 mL of anhydrous ethanol was added. The resultant mixture was centrifuged, washed and dispersed in cyclohexane. The sample obtained was identified to be monoclinic $Ag_2S$ quantum dots by X ray diffraction and transmission electron microscopy, with the particle size below 8 nm, which has a good near-infrared fluorescence emission spectrum. 0.2 g of L-cysteine was added to the above cyclohexane dispersion, then equal volume of anhydrous ethanol was added. The resultant mixture was stirred for 24 h, then centrifuged and washed with deionized water to obtain water-soluble $Ag_2S$ quantum dots with particle sizes of about 8 nm, which still have very strong fluorescence emission. 0.25 mg of the above $Ag_2S$ quantum dots was dispersed in 100 µL of dimethyl sulfoxide (DMSO), and 50 µL of DMSO solution containing 0.01 mmol of NHS was mixed with the above solution. Then 50 µL of DMSO solution containing 0.01 mmol of EDC was added to the above mixed solution. The resultant mixture was packed with aluminum foil, stirred for 1 h, centrifuged and further dispersed in 100 µL of DMSO. The mixed solution of 15 µL of 2 mg/mL Erbitux and 185 µL of 1× PBS was added to 100 µL of $Ag_2S$/DMSO mixed solution. The resultant mixture was reacted in darkness at 4° C. for 12 h, then centrifuged at 400 g for 4 min, and the supernatant was taken. MDA-MB-468 cells were added to the mixed solution of 100 µL of the above supernatant and 100 µL of 1× PBS, coloured at 4° C. for 2 h, and then washed 3 times with 1× PBS solution. It can clearly be seen that the luminescence was given by $Ag_2S$ quantum dots in cells by exciting with 658 nm laser, using 1100 nm filter, and photographing with a 2D InGaAs camera.

EXAMPLE 3

0.1 mmol of silver thiobenzoate, 8 g of hexadecanethiol and 2 g of trioctylphosphine oxide were mixed in a three-necked flask, heated to 160° C. under air for 4 h. After the solution was cooled naturally to room temperature, 50 mL of anhydrous ethanol was added. The resultant mixture was centrifuged, washed and dispersed in cyclohexane. 0.1 g of mercaptopropionic acid was added to the above cyclohexane dispersion, then equal volume of anhydrous ethanol was added. The resultant mixture was vibrated in a vibrator for 8 h, centrifuged and washed with deionized water to obtain water-soluble $Ag_2S$ quantum dots with a particle size of about 6 nm, which still have very strong fluorescence emission. 0.25 mg of the above $Ag_2S$ quantum dots was dispersed in 100 µL of dimethyl sulfoxide (DMSO), and 50 µL of DMSO solution containing 0.01 mmol of NHS was mixed with the above solution. Then 50 µL of DMSO solution containing 0.01 mmol of EDC was added to the above mixed solution. The resultant mixture was packed with aluminum foil, stirred for 1 h, centrifuged and further dispersed in 100 µL of DMSO. The mixed solution of 15 µL of 2 mg/mL Erbitux and 185 µL of 1× PBS was added to 100 µL of $Ag_2S$/DMSO mixed solution. The resultant mixture was reacted in darkness at 4° C. for 12 h, then centrifuged at 400 g for 4 min, and then the supernatant was taken. MDA-MB-468 cells were added to the mixed solution of 100 µL of the above supernatant and 100 µL of 1× PBS, coloured at 4° C. for 2 h, and then washed 3 times with 1× PBS solution. It can clearly be seen that the luminescence was given by $Ag_2S$ quantum dots in cells by exciting with 658 nm laser, using 1100 nm filter, and photographing with a 2D InGaAs camera.

EXAMPLE 4

0.1 mmol of silver hexadecanoate, 5 g of hexadecanethiol and 4 g of octadecylamine were mixed in a three-necked flask and heated to 200° C. under an Ar atmosphere for 1 h. After the solution was cooled naturally to room temperature, 50 mL of anhydrous ethanol was added. The resultant mixture was centrifuged, washed and dispersed in cyclohexane. 0.12 g of mercaptoacetic acid was added to the above cyclohexane dispersion, then equal volume of anhydrous ethanol was added. The resultant mixture was stirred for 24 h, then centrifuged and washed with deionized water to obtain water-soluble $Ag_2S$ quantum dots with a particle size of about 6 nm, which still have very strong fluorescence emission. 0.25 mg of the above $Ag_2S$ quantum dots was dispersed in 100 µL of dimethyl sulfoxide (DMSO), and 50 µL of DMSO solution containing 0.01 mmol of NHS was mixed with the above solution. Then 50 µL of DMSO solution containing 0.01 mmol of EDC was added to the above mixed solution. The resultant mixture was packed with aluminum foil, stirred for 1 h, centrifuged and further dispersed in 100 µL of DMSO. The mixed solution of 15 µL of 2 mg/mL Erbitux and 185 µL of 1× PBS was added to 100 µL of $Ag_2S$/DMSO mixed solution and the resultant mixture was reacted in darkness at 4° C. for 12 h, then centrifuged at 400 g for 4 min, and then the supernatant was taken. MDA-MB-468 cells were added to the mixed solution of 100 µL of the above supernatant and 100 µL of 1× PBS, coloured at 4° C. for 2 h, and then washed 3 times with 1× PBS solution. It can clearly be seen that the luminescence was given by $Ag_2S$ quantum dots in cells by exciting with 658 nm laser, using 1100 nm filter, and photographing with a 2D InGaAs camera.

EXAMPLE 5

0.1 mmol of silver dihydrocarbyldithiophosphate, 10 g eicosanethiol and 4 g of hexadecylamine were mixed in a three-necked flask and heated to 230° C. under an Ar atmosphere for 0.5 h. After the solution was cooled naturally to room temperature, 50 mL of anhydrous ethanol was added. The resultant mixture was centrifuged, washed and dispersed in cyclohexane. 0.1 g of cysteamine was added to the above cyclohexane dispersion, then equal volume of anhydrous ethanol was added. The resultant mixture was stirred for 24 h, then centrifuged and washed with deionized water to obtain water-soluble $Ag_2S$ quantum dots with a particle size of about 5 nm, which still have very strong fluorescence emission. 0.25 mg of the above $Ag_2S$ quantum dots was dispersed in 100 μL of dimethyl sulfoxide (DMSO), and 50 μL of DMSO solution containing 0.01 mmol of NHS was mixed with the above solution. Then 50 μL of DMSO solution containing 0.01 mmol of EDC was added to the above mixed solution. The resultant mixture was packed with aluminum foil, stirred for 1 h, centrifuged and further dispersed in 100 μL of DMSO. The mixed solution of 15 μL of 2 mg/mL Erbitux and 185 μL of 1× PBS was added to 100 μL of $Ag_2S$/DMSO mixed solution, and the resultant mixture was reacted in darkness at 4° C. for 12 h, then centrifuged at 400 g for 4 min, and the supernatant was taken. MDA-MB-468 cells were added to the mixed solution of 100 μL of the above supernatant and 100 μL of 1× PBS, coloured at 4° C. for 2 h, and then washed 3 times with 1× PBS solution. It can clearly be seen that the luminescence was given by $Ag_2S$ quantum dots in cells by exciting with 658 nm laser, using 1100 nm filter, and photographing with a 2D InGaAs camera.

EXAMPLE 6

0.1 mmol of silver dodecanoate, 8 g of octanethiol and 4 g of dodecylamine were mixed in a three-necked flask and heated to 200° C. under an Ar atmosphere for 0.5 h. After the solution was cooled naturally to room temperature, 50 mL of anhydrous ethanol was added. The resultant mixture was centrifuged, washed and dispersed in cyclohexane. 0.12 g of mercaptoacetic acid was added to the above cyclohexane, then equal volume of anhydrous ethanol was added, stirred for 24 h, then the resultant mixture was centrifuged and washed with deionized water to obtain water-soluble $Ag_2S$ quantum dots with a particle size of about 5 nm, which still have very strong fluorescence emission. 0.25 mg of the above $Ag_2S$ quantum dots was dispersed in 100 μL of dimethyl sulfoxide (DMSO), and 50 μL of DMSO solution containing 0.01 mmol of NHS was mixed with the above solution. Then 50 μL of DMSO solution containing 0.01 mmol of EDC was added to the above mixed solution, and the resultant mixture was packed with aluminum foil, stirred for 1 h, centrifuged and further dispersed in 100 μL of DMSO. The mixed solution of 15 μL of 2 mg/mL Erbitux and 185 μL of 1× PBS was added to 100 μL of $Ag_2S$/DMSO mixed solution, and the resultant mixture was reacted in darkness at 4° C. for 12 h, and then centrifuged at 400 g for 4 min, and the supernatant was taken. MDA-MB-468 cells were added to the mixed solution of 100 μL of the above supernatant and 100 μL of 1× PBS, coloured at 4° C. for 2 h, and then washed 3 times with 1× PBS solution. It can clearly be seen that the luminescence was given by Ag2S quantum dots in cells by exciting with 658 nm laser, using 1100 nm filter, and photographing with a 2D InGaAs camera.

In conclusion, the method of the invention has moderate reaction conditions, simple operation, short production cycle, good reproducibility, and is easy to control. The as-prepared $Ag_2S$ quantum dots have high fluorescence yield, good fluorescence stability, excellent biocompatibility and homogeneous sizes, and can well be used for cellular imaging and in vivo animal tissue imaging. Furthermore, the method of the present invention is easy to be implemented in large scale, thus is applicable for the industrial production.

The above examples are only the representative ones of numerous examples of the invention, and do not limit the protection scope of the invention at all. All the technical solutions having the equivalent variations or equivalent substitutions fall within the protection scope of the invention.

The invention claimed is:

1. A method for preparation of near-infrared silver sulfide quantum dots, characterized in that the method comprises the following steps:
   1) preparing hydrophobic silver sulfide quantum dots; and
   2) reacting the hydrophobic silver sulfide quantum dots in step 1) with stoichiometric or excessive amount of mercapto-containing hydrophilic reagent in polar organic solvent to allow the surface thereof to be attached with hydrophilic groups, so as to obtain the hydrophilic near-infrared silver sulfide quantum dots;
   the hydrophilic reagent is any one of mercaptopropionic acid, cysteine, cysteamine, thioctic acid and ammonium mercaptoacetate or any combination thereof;
   wherein the step 1) comprises the following steps:
   1-1) heating a mixed reaction system containing a silver source and a long chain thiol to 80-350° C. in a closed environment, to react sufficiently; and
   1-2) naturally cooling the mixed reaction system to room temperature and then adding a polar solvent, centrifuging and washing to obtain the hydrophobic near-infrared silver sulfide quantum dots;
   wherein the silver source comprises one or more of silver nitrate, silver diethyldithiocarbamate, silver dihydrocarbyldithiophosphate, dioctyl silver sulfosuccinate, silver thiobenzoate, silver acetate, silver dodecanoate, silver tetradecanoate and silver octadecanoate;
   the long chain thiol comprises one or more of octanethiol, undecanethiol, dodecanethiol, tridecanethiol, tetradecanethiol, pentadecanethiol, hexadecanethiol, octadecanethiol, eicosanethiol, hexanethiol, 1,6-hexanedithiol, and 1,8-octanedithiol;
   wherein in step 2), the hydrophobic silver sulfide quantum dots are reacted with the mercapto-containing hydrophilic reagent in the polar organic solvent at 2-80° C. for 3 or more hours; and
   wherein in step 1-2), the mixed reaction system further comprises a surfactant having coordination property, selected from the group consisted of a long chain alkyl acid, alkylamine, a long chain alcohol, and ether or any combination thereof, the mixed reaction system is placed in a closed environment to react.

2. The method for preparation of near-infrared silver sulfide quantum dots according to claim 1, characterized in that in step 2), the pH value of the reaction system is adjusted to 7-14.

3. The method for preparation of near-infrared silver sulfide quantum dots according to claim 1, characterized in that in step 2), the polar organic solvent comprises any one or more of ethanol, methanol, acetone and 1-methyl-2-pyrrolidone.

4. The method for preparation of near-infrared silver sulfide quantum dots according to claim 1, characterized in that in step 2), the hydrophobic silver sulfide quantum dots are reacted with the mercapto-containing hydrophilic reagent under the condition of continuous stirring and/or vibrating and/or sonicating in the polar organic solvent at 2-80° C. for 3 or more hours.

\* \* \* \* \*